Figure 1:
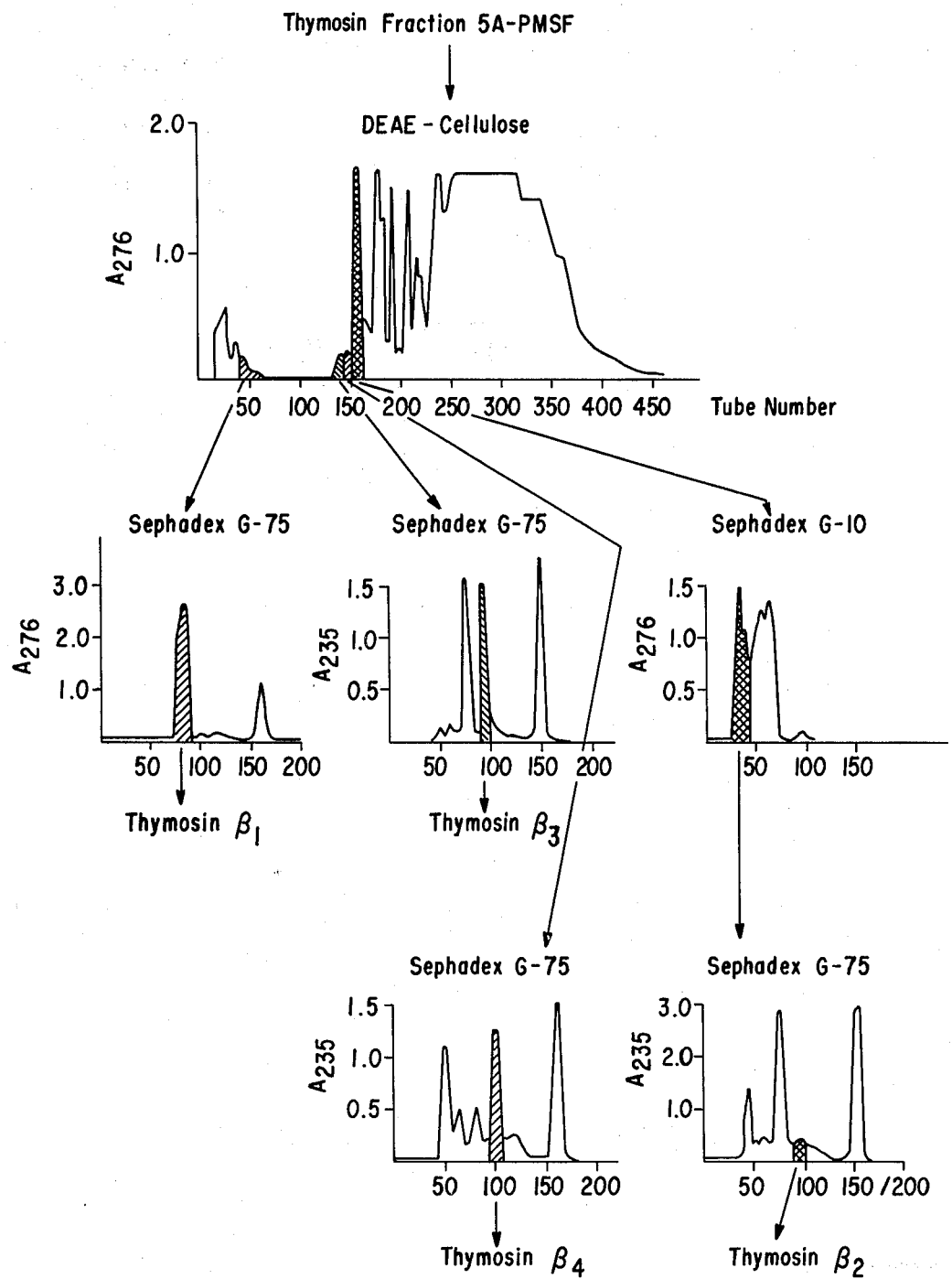

United States Patent [19]

Goldstein et al.

[11] 4,297,276

[45] Oct. 27, 1981

[54] THYMOSIN BETA 3 AND BETA 4

[75] Inventors: Allan L. Goldstein, Washington, D.C.; Teresa L. K. Low, Annandale, Va.

[73] Assignee: Hoffman-La Roche Inc., Nutley, N.J.

[21] Appl. No.: 159,430

[22] Filed: Jun. 16, 1980

Related U.S. Application Data

[63] Continuation-in-part of Ser. No. 23,115, Mar. 23, 1979, abandoned, which is a continuation-in-part of Ser. No. 967,675, Dec. 8, 1978, abandoned.

[51] Int. Cl.$^3$ .................... C07C 103/52; A61K 37/00
[52] U.S. Cl. .............................. 260/112.5 R; 424/177
[58] Field of Search ................. 260/112.5 R; 424/177

[56] References Cited

U.S. PATENT DOCUMENTS 4,079,127  3/1978  Goldstein et al. ........... 260/112.5 R

*Primary Examiner*—Delbert R. Phillips
*Attorney, Agent, or Firm*—Jon S. Saxe; George M. Gould; John B. Wilson

[57] ABSTRACT

Two related polypeptides, thymosin $\beta_3$ and thymosin $\beta_4$, have been isolated from Thymosin fraction 5. These peptides have been characterized and sequenced. Thymosin $\beta_3$ has 50 amino acid residues while thymosin $\beta_4$ has 43 amino acid residues corresponding identically to the amino terminal 43 amino acids of thymosin $\beta_3$. The compounds have useful biological activity as evidenced by their ability to induce terminal deoxynucleotidyl transferase (TdT) positive cells in T-cell populations. The invention described herein was made in part in the course of work under a grant or award from the Department of Health, Education and Welfare.

2 Claims, 3 Drawing Figures

THYMOSIN BETA 3 AND BETA 4

RELATED APPLICATIONS

This application is a continuation-in-part of copending application Ser. No. 23,115, filed Mar. 23, 1979, now abandoned which is a continuation-in-part of Ser. No. 967,675, filed Dec. 8, 1978, now abandoned.

BACKGROUND OF THE INVENTION

The isolation and characterization of a peptide component of thymosin fraction 5 termed thymosin $\alpha_1$, was described in U.S. Pat. No. 4,079,127. Thymosin $\alpha_1$ contained 28 amino acid residues and was an acidic peptide having a pI of about 4.0–4.3. It is further distinguished in having a blocked amino terminal (N-acetyl). Biologically thymosin $\alpha_1$ is active in the MIF, E-rosette and mitogen assays but is not active in the mixed lymphocyte response (MLR) assay. The amino acid sequence for thymosin $\alpha_1$ is as follows:

(N-acetyl)-Ser-Asp-Ala-Ala-Val$^5$-Asp-Thr-Ser-Ser-Glu$^{10}$-Ile-Thr-Thr-Lys-Asp$^{15}$ Leu-Lys-Glu-Lys-Lys$^{20}$-Glu-Val-Val-Glu-Glu$^{25}$-Ala-Glu-Asn-OH Goldstein et al., J. of Reticuloendothelial Society 23, 253 (1978) described partially purified thymosin $\beta_3$ and $\beta_4$ as components of thymosin fraction 5 and gross physical data is given. Additionally, Low and Goldstein in Year In Hematology 1978, Siber et al. ed. (Plenum Pub. Co. 1978) at p. 281 indicated that partially purified thymosin $\beta_3$ and $\beta_4$ induce TdT positive cells in T-cell populations.

The sequence for thymosin $\beta_3$ and $\beta_4$ advanced in the parent application, Ser. No. 967,675, has been revised in amino acids 24–35 by exchanging original sequence 30–35 for original sequence 24–29 of both peptides. This revision is based on additional data derived from thermolysin digests used in the peptide mapping.

DESCRIPTION OF THE INVENTION

The present invention relates to the isolation and chemical characterization of thymosin $\beta_3$ and $\beta_4$. Thymosin $\beta_3$ has an isoelectric point of 5.2 and a molecular weight of 5,500. Thymosin $\beta_4$ has an isoelectric point of 5.1 and molecular weight of 4,982. They are the only two polypeptides isolated from fraction 5 thus far that can induce TdT positive cells. The induction of TdT by thymosin fraction 5 exhibits a bell shaped dose response curve. However, TdT response to thymosin $\beta_3$ and $\beta_4$ increases as the doses increase. The amino acid sequences for thymosin $\beta_3$ and $\beta_4$ are as follows:

Sequence of Thymosin $\beta_3$ $$CH_3-\overset{\overset{\displaystyle O}{\|}}{C}-Ser-Asp-Lys-Pro-Asp^5-Met-Ala-Glu-Ile-Glu^{10}$$

-Lys-Phe-Asp-Lys-Ser$^{15}$-Lys-
-Leu-Lys-Lys-Thr$^{20}$-Glu-Thr-Gln-Glu-Lys$^{25}$-Asn
-Pro-Leu-Pro-Ser$^{30}$-Lys-Glu-Thr-Ile-Glu$^{35}$-Gln-Glu-
-Lys-Gln-Ala$^{40}$-Gly-Glu-Ser-(Asx, Glx, Ile,Thr)Ala-Lys-Thr-OH

Sequence of Thymosin $\beta_4$ $$CH_3-\overset{\overset{\displaystyle O}{\|}}{C}-Ser-Asp-Lys-Pro-Asp^5-Met-Ala-Glu-Ile-Glu^{10}$$

-Lys-Phe-Asp-Lys-Ser$^{15}$-Lys-
-Leu-Lys-Lys-Thr$^{20}$-Glu-Thr-Gln-Glu-Lys$^{25}$-Asn
-Pro-Leu-Pro-Ser$^{30}$-Lys-Glu-Thr-Ile-Glu$^{35}$-Gln-Glu-
-Lys-Gln-Ala$^{40}$-Gly-Glu-Ser-OH

Thymosin $\beta_3$ and $\beta_4$ were isolated from fraction 5A-PMSF by a combination of ion-exchange chromatography and gel filtration. Thymosin fraction 5A-PMSF was prepared according to the procedures as for thymosin fraction 5 (Hooper, et al., N.Y. Acad. Sci. 249, 125, 1975) with the following modifications. Protease inhibitor phenylmethylsulfonyl fluoride (PMSF) was added to the homogenizing media at a concentration of 0.1 mM. After the acetone precipitation, a 50–95% ammonium sulfate precipitation cut was made and was processed through ultrafiltration on DC-2 hollow fiber system and gel filtration on Sephadex G-25. The resulting protein peak was collected and was designated thymosin fraction 5A-PMSF. As summarized in FIG. 1, thymosin $\beta_3$ and $\beta_4$ were derived from thymosin fraction 5A-PMSF. Lyophilized thymosin fraction 5A-PMSF was chromatographed on a column packed with DEAE-cellulose in 10 mM Tris, 1 mM 2-mercaptoethanol, pH 8.5. Two stepwise linear gradients of 0–0.5 M NaCl and 0.5–1.0 M NaCl were used for the elution.

Thymosin $\beta_3$ was derived from the first retained peak and $\beta_4$ from the second retained peak of the DEAE-cellulose column. They were further purified by gel filtration on Sephadex G-75 in 6 M guanidine hydrochloride. The yield of thymosin $\beta_3$ from fraction 5 is about 1.7% and $\beta_4$ about 1.6%. Both preparations are free of carbohydrate and nucleotide.

Isoelectric focusing was conducted for 90 minutes using a constant power of 25 watts (LKB Model 2103 power supply). The gels were fixed in 20% trichloroacetic acid for one hour. They were stained in 0.1% Coomassie Blue in 20% trichloroacetic acid and destained in 10% trichloroacetic acid.

It should be noted that $\beta_3$ and $\beta_4$ failed to be stained with either isopropanol staining procedure as used for thymosin $\alpha_1$ as set forth in U.S. Pat. No. 4,079,127 or the LKB procedure which uses sulfosalicylic acid, methanol and trichloroacetic acid in the staining solution.

For amino acid analysis, samples were hydrolyzed in 6 N HCl in evacuated sealed tubes for 24–120 hours at 110°. Amino acid analyzers used include a Beckman Model 119, a Beckman Model 121M, Beckman Model 119CL and a JEOL Model JLC-6AH. Thymosin $\beta_3$ and $\beta_4$ were also hydrolyzed with 3 N mercaptoethanesulfonic acid (Anal. Biochem. 60:45 (1974). Six normal hydrochloric acid containing 0.21 M dimethylsulfoxide (Anal. Biochem. 32:185 (1969)) was used for hydrolysis to determine content of cysteine or cystine.

Enzymatic digestion was performed in 1% ammonium bicarbonate at pH 8.3 for 2 to 3 hours at 37°. Trypsin or chymotrypsin were added to the protein solution for a final enzyme-substrate ratio of 1:50 (w/w). Cyanogen bromide cleavage was performed in 70% formic acid at room temperature for 4 hours. The ratio of cyanogen bromide to protein is 5:1 (w/w).

Cyanogen bromide was added in equal portions to the protein solution with stirring at intervals of one hour. At the end of four hours, the reaction product was diluted with five volumes of distilled water and lyophilized.

Partial acid hydrolysis was achieved in 0.03 M HCl at 110° for 4 to 16 hours in sealed evacuated tubes.

Separation of enzymatic digests or partial acid hydrolysis products of thymosin $\beta_3$ or $\beta_4$ was performed largely by paper electrophoresis and/or chromatography. In a two-dimensional separation, paper chromatography was carried out first, with n-butanol:glacial acetic acid:water=4:1:5 (v/v). This was followed by high-voltage electrophoresis at pH 1.9 for 30–50 minutes at 60 volts/cm. Peptides were detected with cadmium-ninhydrin reagent or with fluorescamine in acetone.

Figure 2:
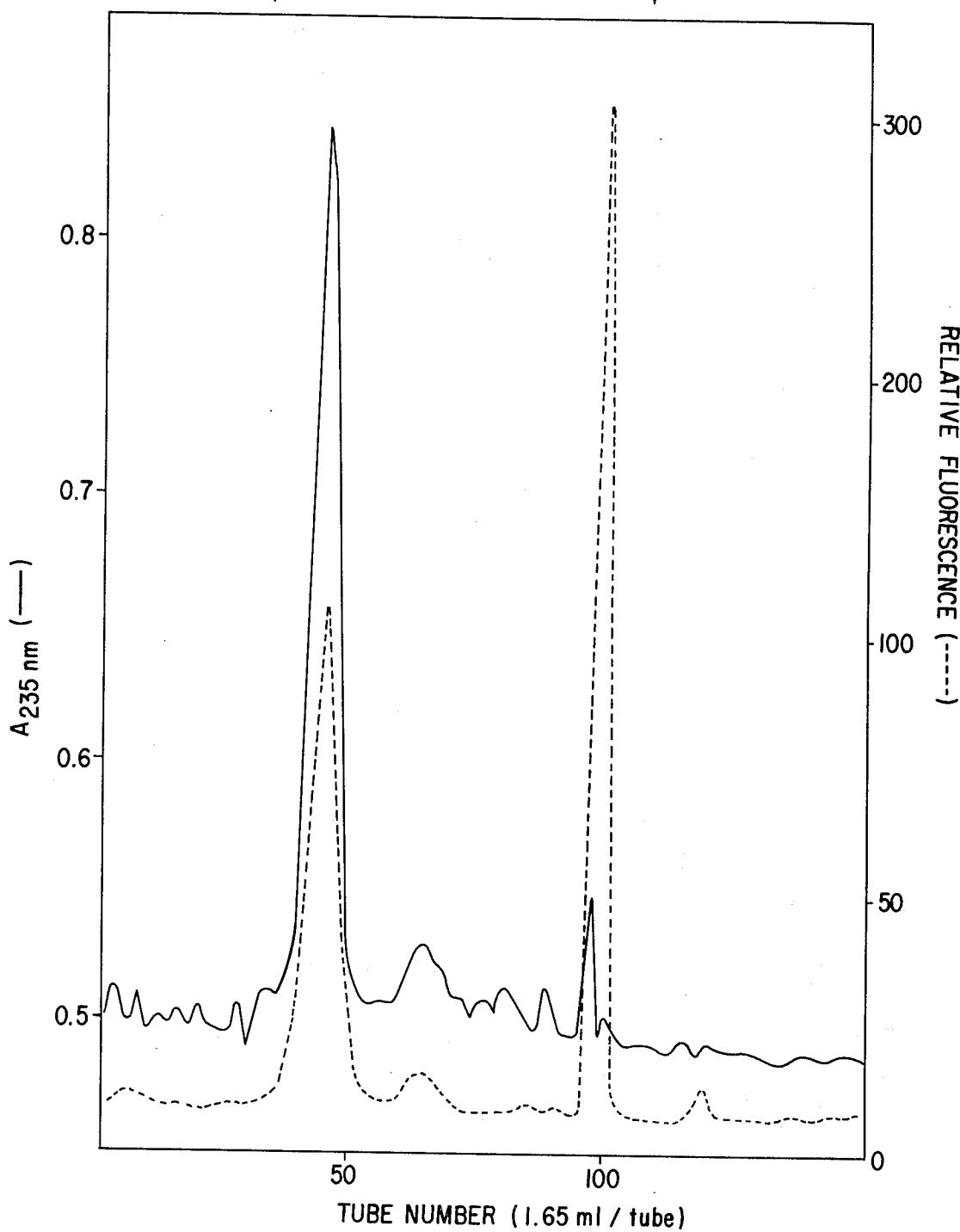

Separation of cyanogen bromide cleavage products was accomplished by gel filtration on Sephadex G-50 in 0.1 M NH$_4$OH as shown in FIG. 2. Effluents were monitored by absorbance at 235 nm as well as by fluorescamine assay after alkaline hydrolysis as described by Nakai, et al. (Anal. Biochem. 58:563 (1974)). Peak 2 (CNBr fragment 1) was further purified by high-voltage paper electrophoresis at pH 1.9.

The amino acid sequence of the separated peptides were determined by Edman degradation procedures. The presence of amide groups on a peptide was deduced from the latter's mobility on high-voltage paper electrophoresis at pH 6.5.

Table 1 shows the amino acid composition of and the amino acid sequence as shown on page 3. Thymosin $\beta_3$ and $\beta_4$ have very similar amino acid composition except that $\beta_3$ is larger and contains seven extra residues than $\beta_4$.

TABLE 1

Amino Acid Composition of Thymosin $\beta_3$ and $\beta_4$

| Amino Acid | $\beta_3$ | $\beta_4$ |
| --- | --- | --- |
| Lysine | 11.35(11) | 8.71(9) |
| Histidine | 0.00(0) | 0.00(0) |
| Arginine | 0.00(0) | 0.00(0) |
| Aspartic | 4.91(5) | 4.73(4) |
| Threonine | 4.68(5) | 2.62(3) |
| Serine | 3.91(4) | 3.73(4) |
| Glutamic | 13.70(14) | 12.10(11) |
| Proline | 3.89(4) | 4.85(3) |
| Glycine | 1.10(1) | 1.35(1) |
| Alanine | 2.25(2) | 2.30(2) |
| Valine | 0.00(0) | 0.37(0) |
| Methionine | 0.52(1) | 0.31(1) |
| Isoleucine | 2.35(2) | 1.85(2) |
| Leucine | 2.58(3) | 2.05(2) |
| Tyrosine | 0.00(0) | 0.00(0) |
| Phenylalanine | 1.15(1) | 0.85(1) |
| Total | 53 | 43 |
| MW | 5,500 | 4,982 |
| pI | 5.2 | 5.1 |
| Asp + Glu (%) | 35.2 | 34.9 |

Digestion of thymosin $\beta_4$ with trypsin produces 16 peptides. Table 2 lists their amino acid composition.

TABLE 2

Amino Acid Composition of Tryptic Peptides of Thymosin $\beta_4$

| Amino Acid | T1 | T1.2 | T3 | T4 | T5 | T6 | 6.1 | 8 |
| --- | --- | --- | --- | --- | --- | --- | --- | --- |
| Lysine | 2.14(2) | 1.00(1) | 1.26(1) | 2.00(2) | 1.86(2) | 0.99(1) | 0.97(1) | 1.03(1) |
| Histidine | | | | | | | | |
| Arginine | | | | | | | | |
| Aspartic acid | | | | | 0.87(1) | | 0.61(1) | |
| Threonine | | | | 1.64(2) | 0.95(1) | 1.71(2) | 0.86(1) | 0.93(1) |
| Serine | | | 0.84(1) | | 1.31(1) | 0.50 | 1.08(1) | |
| Glutamic acid | | | | 3.14(3) | 2.42(2) | 3.07(3) | 2.03(2) | 3.87(4) |
| Proline | | | | | 0.66(1) | | 0.72(1) | |
| Glycine | | | | | 0.87(1) | | 0.57 | |
| Alanine | | | | | 0.46 | | 0.30 | |
| Valine | | | | | 0.21 | | | |
| Methionine | | | | | | | | |
| Isoleucine | | | | | | | | 0.86(1) |
| Leucine | 0.84(1) | | | | 0.29 | | 0.31 | |
| Tyrosine | | | | | | | | |
| Phenylalanine | | | | | | | | |
| Total | 3 | 1 | 3 | 7 | 9 | 6 | 7 | 7 |
| N terminal (dansyl) | Leu | | Ser | Lys | Ser | Thr=Ser | Asx | Glx |

| Amino Acid | T9 | T9.1 | T10 | T11 | T13 | T14 | T16 |
| --- | --- | --- | --- | --- | --- | --- | --- |
| Lysine | 1.10(1) | 0.96(1) | 1.07(1) | 1.01(1) | 2.25(2) | | 1.10(1) |
| Histidine | | | | | | | |
| Arginine | | | | | | | |
| Aspartic acid | 1.07(1) | 3.06(3) | 0.97(1) | | 2.09(2) | | 1.17(1) |
| Threonine | | | | | | | |
| Serine | 0.98(1) | 0.85(1) | | | 0.95(1) | 0.97(1) | 0.93(1) |
| Glutamic acid | | 2.00(2) | | | 2.18(2) | 2.34(2) | 0.76(1) |
| Proline | 1.85(2) | 1.03(1) | | | 1.10(1) | | |
| Glycine | | | | | | 1.02(1) | 0.75(1) |
| Alanine | | 0.96(1) | | | 0.80(1) | 1.04(1) | 0.24 |
| Valine | | | | | | | |
| Methionine | | | | | 0.79(1) | | |
| Isoleucine | | 1.09(1) | | | 0.91(1) | | |
| Leucine | 0.79(1) | | | 0.83(1) | | | |
| Tyrosine | | | | | | | |
| Phenylalanine | | 0.91(1) | 0.87(1) | | | | 0.87(1) |
| Total | 6 | 11 | 3 | 2 | 11 | 5 | 6 |
| N terminal (dansyl) | Asx | | Phe | Leu | | Glx | | approximate molecular weight (MW) based on an approximate number of amino acid residues in thymosin $\beta_3$. The molecular weight and number of amino acid residues in thymsin $\beta_4$ are based on the established These peptides have been sequenced and the location of acids or amides assigned. These data, along with results obtained from cyanogen bromide cleavage of thymosin $\beta_4$ as well as partial acid hydrolysis of CNBr fragment 1, established the sequence of N-terminal 14-residue of thymosin $\beta_4$ as follows:

Blocked-Ser-Asp-Lys-Pro-Asp-Met-Ala-Glu-Ile-Glu-Lys-Phe-Asp-Lys

The N-terminal end of this 14-residue peptide as well as the intact thymosin $\beta_4$ are blocked. Other tryptic peptides isolated and sequenced are listed below:

T9: Asn-Pro-Leu-Pro-Ser-Lys
T4: Lys-Thr-Glu-Thr-Gln-Glu-Lys
T6: Thr-Glu-Thr-Gln-Glu-Lys
T8: Glu-Thr-Ile-Glu-Gln-Glu-Lys
T14: Gln-Ala-Gly-Glu-Ser

Tryptic peptide map of thymosin $\beta_3$ appeared very similar to that of thymosin $\beta_4$. The only differences are that peptide T14 of $\beta_4$ was missing from the map of $\beta_3$ and an extra peptide was shown on $\beta_3$ map with the amino acid composition of (Asx, Thr$_2$,Ser,Glx$_3$,Gly,Ala$_2$,Ile,Lys).

Thus, it is seen that $\beta_3$ and $\beta_4$ have identical sequence at the N-terminal end of 43 residues and are differed at the C-terminal ends.

In order to completely elucidate the sequence of $\beta_3$ and $\beta_4$, $\beta_4$ was digested with thermolysin and separated on a Bio-gel P-4 column in 0.1 M NH$_4$OH. The separated pools were further fractionated on paper. Table 2a lists the amino acid composition of the isolated thermolysin peptides. These peptides were partially sequenced to provide overlaps for the tryptic peptides.

Additional tryptic digests of $\beta_3$ have provided the following peptides:

GR T 12 H Asx, Ser, Glx, Pro, Gly, Leu, Lys
GR T 13 H Glx, Gly, Ala

Further thermolysin digests of $\beta_3$ provided the following peptides:

GS 3H Asx, Thr, Ser, Glx$_2$, Gly, Ala, Leu, Lys
GS 4G Leu(Lys, Lyd, Thr)
GS 8G Asx, Thr, Glx$_3$, Lys

Based on GS 4G and GS 8G, peptide T 9 could be placed in the sequence at #30–35 while peptide T$_6$ is positioned in the sequence at #24–29. The full sequences for $\beta_3$ and $\beta_4$ reflect these assignments. Peptides GR T 12 H, GR T 13 H and GS 3H are believed to represent the C-terminal of $\beta_3$.

TABLE 2a

| Amino Acid Composition of Thermolysin Peptides of Thymosin $\beta_4$ | | | | | | | | | |
|---|---|---|---|---|---|---|---|---|---|
| Amino Acid | Th 1 | Th 1 T 1 | Th 1 T 2 | Th 2 | Th 2 T 1 | Th 2 T 2 | Th 2 T 3 | Th 2 T 4 | Th 2 T 5 |
| Lysine | 2.04(2) | 0.94(1) | 1.00(1) | 4.14(4) | 2.12(2) | 1.14(1) | 0.98(1) | 2.26(2) | 1.01(1) |
| Histidine | | | | | | | | | |
| Arginine | | | | | | | | | |
| Aspartic acid | 0.97(1) | | 1.06(1) | 1.03(1) | | | 1.07(1) | 1.10(1) | |
| Threonine | | | | 2.94(3) | | | | 2.00(2) | 1.82(2) |
| Serine | 1.02(1) | 0.96(1) | | 1.20(1) | | | 0.98(1) | 1.20(1) | |
| Glutamic acid | | | | 4.04(4) | | | | 3.17(3) | 2.73(3) |
| Proline | | | | 2.20(2) | | | 1.45(2) | 1.60(2) | |
| Glycine | | | | | | | | | |
| Alanine | | | | | | | | | |
| Valine | | | | | | | | | |
| Methionine | | | | | | | | | |
| Isoleucine | | | | | | | | | |
| Leucine | | | | 2.02(2) | 0.87(1) | 0.89(1) | 0.94(1) | 0.71(1) | |
| Tyrosine | | | | | | | | | |
| Phenylalanine | 0.98(1) | | 0.93(1) | | | | | | |
| Total | 5 | 2 | 3 | 17 | 3 | 2 | 6 | 12 | 6 |
| N-terminal (dansyl) | Phe | | | Leu | | | Asx | | |

| Amino Acid | Th 2 T 6 | Th 3 | Th 5 | Th 6 | Th 9 | Th 10 |
|---|---|---|---|---|---|---|
| Lysine | | | 0.85(1) | 0.84(1) | 0.90(1) | 2.25(2) |
| Histidine | | | | | | |
| Arginine | | | | | | |
| Aspartic acid | | | | | | 2.04(2) |
| Threonine | 0.91(1) | | | | | 1.02(1) |
| Serine | | | 0.97(1) | 0.96(1) | | |
| Glutamic acid | 1.09(1) | 1.07(1) | 4.10(5) | 3.21(3) | 1.31(1) | 2.02(2) |
| Proline | | | | | | 1.20(1) |
| Glycine | | | 1.12(1) | 1.04(1) | | |
| Alanine | | | 1.02(1) | 0.97(1) | | 1.03(1) |
| Valine | | | | | | |
| Methionine | | | | | | 0.56(1) |
| Isoleucine | | | 0.62(1) | 0.62(1) | 0.67(1) | 0.86(1) |
| Leucine | | | | | | |
| Tyrosine | | | | | | |
| Phenylalanine | | | | | | |
| Total | 2 | 4 | 10 | 5 | 3 | 11 |
| N-terminal (dansyl) | | | Ile | | | |

Partial acid hydrolysis of $\beta_4$ gave rise to several useful peptides for overlapping. The amino acid composition of these peptides are listed in Table 2b.

TABLE 2b

Amino Acid Composition of Peptides Obtained by Partial and Hydrolysis of Thymosin $\beta_4$

| Amino Acid | P 1 | P 1 T 1 | P 1 T 2 | P 1 T 3 | P 1 T 5 | P 2 | P 3 | P 4 | P 8 |
| --- | --- | --- | --- | --- | --- | --- | --- | --- | --- |
| Lysine | 5.01(5) | 2.20(2) | 2.04(2) | 1.0(1) | 2.10(2) | 1.10(1) | | | 1.07(1) |
| Histidine | | | | | | | | | |
| Arginine | | | | | | | | | |
| Aspartic acid | | | | | | | | 1.00(1) | |
| Threonine | 1.45(2) | 1.68(2) | | | | | | | |
| Serine | 1.26(1) | | | | 0.70(1) | | 1.00(1) | | |
| Glutamic acid | 2.81(3) | 3.08(3) | | | | | | | 2.02(2) |
| Proline | | | | | | 0.70(1) | | | |
| Glycine | | | | | | | | | |
| Alanine | | | | | | | | | 0.82(1) |
| Valine | | | | | | | | | |
| Methionine | | | | | | | | | 0.80(1) |
| Isoleucine | | | | | | | | | 1.02(1) |
| Leucine | 0.99(1) | | 0.91(1) | | | | | | |
| Tyrosine | | | | | | | | | |
| Phenylalanine | | | | | | | | | 1.06(1) |
| Total | 12 | 7 | 3 | 1 | 3 | 2 | 1 | 1 | 7 |

Sequencer Run of Thymosin $\beta_3$

A sample of the cyanogen bromide (CNBr) clearage product of thymosin $\beta_3$ was applied to a sequencer (Beckman 890 c). The sample was precoupled with sulfophenylisothiocyanate (3-SPITC) in the reaction cup before the sequencer program was initiated. Beckman DMAA program (peptide program 102974) was used. The sequencer products were identified by high performance liquid chromatograph (HPLA) in a Hewlett Packard 1084B and/or analyzed by amino acid analysis after backhydrolysis with hydriodic acid. The results which are in total agreement with data obtained by manual sequence techniques are as follows:

Met-(ALA)-Glu-Ile-Glu-Lys-Phe-Asp-Lys-Ser-Lys-Leu-Lys-Lys-Thr-Glu-Thr-Gln-Glu-Lys-Asn-Pro-Leu-Pro-Ser-Lys-Glu-Thr-Ile-Glu-Gln-Glu-Lys-Gln-Ala-Gly-( )-( )-Asx.

The first residue was not identifiable since the peptide was modified with 3-SPITC prior to the sequencer run. The overall sequencers for thymosin $\beta_4$ and $\beta_3$ are as follows:

Amino Acid Sequence of Thymosin Beta 4

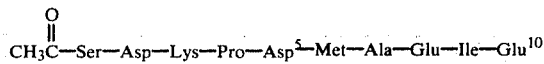

-Lys-Phe-Asp-Lys-Ser$^{15}$-Lys-Leu-Lys-Lys-Thr$^{20}$-Glu-Thr-Gln-Glu-Lys$^{25}$-Asn-Pro-Leu-Pro-Ser$^{30}$-Lys-Glu-Thr-Ile-Glu$^{35}$-Gln-Glu-Lys-Gln-Ala$^{40}$-Gly-Glu-Ser-OH.

Amino Acid Sequence of Thymosin Beta 3

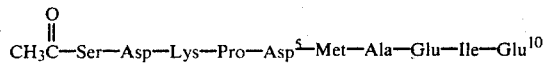

-Lys-Phe-Asp-Lys-Ser$^{15}$-Lys-Leu-Lys-Lys-Thr$^{20}$-Glu-Thr-Gln-Glu-Lys$^{25}$-Asn-Pro-Leu-Pro-Ser$^{30}$-Lys-Glu-Thr-Ile-Glu$^{35}$-Gln-Glu-Lys-Gln-Ala$^{40}$-Gly-Glu-Ser-(Asx, Glx$^{45}$, Ile, Thr)Ala-Lys-Thr$^{50}$-OH.

Although considerable research has dealt with the differentiation of immunologically mature T cells, few studies have addressed the control of differentiation of early T cells. The progression of T cell differentiation is thought to begin in the bone marrow. Further maturation then occurs in the thymus and terminally differentiated T cells localize in peripheral lymphoid tissues. This sequence of differentiation has been indicated primarily by ablation and reconstitution types of experiments, since specific markers for early thymocytes have been difficult to identify.

During the last few years, however, several studies have indicated that the enzyme terminal deoxynucleotidyl transferase (TdT) is uniquely associated with early T cell differentiation. In vitro, TdT polymerizes deoxynucleotides and although it requires a primer, it does not require a template. The function of the enzyme in vivo, however, is not known. TdT is found in the cortisone-sensitive, major thymus population, but not in immunologically committed, more mature T cells. Low levels of TdT are also found in bone marrow cells and this activity has been shown to be localized in a minor cell population separable by BSA gradient fractionation. This population of prothymocytes is Thy-1-negative, but can be induced in vitro to express Thy-1 by thymic hormones. In previous studies and in the results obtained herein the factors that control the differentiation of this prothymcyte population have been examined. The results demonstrate that the thymic hormone, $\beta_3$ and the related peptide $\beta_4$ induce TdT in an early prothymocyte population in bone marrow from athymic mice, demonstrating the thymic regulation of early prothymocyte differentiation in the bone marrow.

NIH Swiss nu/+, nu/nu and C57BL/6 specific pathogen-free mice used in the present experiments were obtained from the Frederick Cancer Research Center's Animal Production Area, Frederick, Maryland. Mice were 6 weeks old at the beginning of the experiments.

The method of Raidt et al., J. Exp. Med. 128, 681 (1968) was used to fractionate different cell suspensions from spleen, thymus, lymph nodes or bone marrow. Four layers of cells were formed at the interfaces of the discontinuous BSA gradient: Fraction A between 10% and 23% BSA; fraction B between 23–26%; fraction C between 26–29%; and fraction D between 29–33% BSA. BSA (Path-O-Cyte 5, lots 25 and 26) was obtained from Miles Research Products (Elkhart, Ind.). Fractionated cells were washed three times in Ham's F-12 medium.

The procedure for enzyme extraction has been described previously by Pazmino et al., J. Immunol. 119, 494 (1977).

The TdT assay was adapted from Kung et al, J. Exp. Med. 141, 855 (1975). One unit of enzyme activity was defined as the amount catalyzing the incorporation of 1 pmol of dGTP into acid insoluble material per hour. The specific activity was calculated from the total enzyme activity recovered from phosphocellulose per $10^8$ nucleated viable cells.

Rabbit anti-Thy-1 serum was prepared by injecting $1 \times 10^7$ thymocytes from B6C3F$_1$ mice three times at weekly intervals. The rabbit was bled two weeks after the last injection. The serum was decomplemented and absorbed on B6C3F$_1$ liver cells twice and on NIH Swiss nu/nu spleen cells three times.

The indirect immunofluorescence method of Cerottini and Brunner, Immunology 13, 395 (1967) was used to determine the frequency of Thy-1-positive cells. BSA-fractionated bone marrow cells, which had or had not been incubated with thymosin (50 ng/ml) for two hours at 37° C., were incubated with rabbit anti-Thy-1 serum (1:200) at 37° C. for 30 minutes. The cells were centrifuged and washed three times in cold Ham's F-12 medium. The washed cells were suspended in 0.10 ml of a fivefold dilution of fluorescein-conjugated goat anti-rabbit IgG (Meloy Laboratories, Springfield, Va.) and incubated at room temperature for 30 minutes. The cells were washed twice with Ham's F-12 medium and resuspended in a drop of Bacto FA mounting fluid, pH 7.2 (Difco Laboratories, Detroit, Mich.). Smears of cells were made on the surface of microscope slides and then were examined by fluorescence microscopy.

Thymosin fraction 5 (Lot No. BPM390) and spleen fraction 5 (Lot No. 307), purified as previously described by Hooper et al. Ann. N.Y. Acad. Sci. 249, 175 (1975), were resuspended in saline solution at a concentration of 500 μg/ml.

Ten daily injections of 100 μg were given intraperitoneally to six-week-old NIH Swiss nu/nu, which were sacrificed 24 hours after the last injection. For the in vitro induction experiments, cells were washed three times after BSA gradient fractionation in Ham's F-12 medium containing 100 U/ml penicillin, 100 μg/ml streptomycin and 10 μg/ml gentomycin. After being washed, cell concentrations were adjusted to $1 \times 10^8$ cells/dish in 20 ml of Ham's F-12 medium containing antibiotics, 5% fetal bovine serum (Flow Laboratories, Rockville, Md.) and different concentrations of thymosin or spleen fraction 5 or of any of the different peptides isolated from thymosin. After incubation for various periods of time, cells were collected, washed twice with Ham's F-12 and extracted as previously described for TdT activity.

The following peptides, isolated from thymosin, were assayed for their ability to induce TdT in vitro: $\alpha_1$, $\beta_1$, $\beta_3$, $\beta_4$, and synthetic $\alpha$-1.

Actinomycin D at 0.5 μg/ml was incubated for 12 hours in the presence of thymosin with fraction B from the bone marrow of NIH Swiss nu/nu mice to study their effect on TdT induction. To follow the effect of Actinomycin D on RNA synthesis, cells were labeled with [$^3$H] uridine (10 μCi/ml) for the last 90 minutes of incubation.

In order to better assess the distribution of TdT in these tissues, thymus and bone marrow cell populations from NIH Swiss mice fractionated on discontinous BSA gradients were examined for TdT activity.

Thymosin activity was also tested by a in vivo TdT assay. Different doses of thymosin fraction 5 and other purified thymosin polypeptides were injected into hydrocortisone acetate treated C57BL/6J mice daily for 9 to 11 days. The animals were sacrificed, thymocytes prepared and TdT activity determined using the method described by Pazmino et al., J. Immunol. 119, 494 (1977). The ability of thymosin to induce the differentiation of pre-T cells to TdT positive thymocytes was demonstrated by the higher level of TdT activity, i.e., by increasing the number of TdT positive thymocytes. Table 2c gives the results of a typical TdT assay in vivo. One μg of $\beta_3$ is as active in inducing TdT in vivo as 100 μg of thymosin fraction 5.

TABLE 2c

In Vivo Induction of TdT in Thymocytes From Hydrocortisone Acetate Treated C57BL/6J Mice

| Treatment | TdT Specific Activity* |
|---|---|
| Control saline | 836.3 |
| Spleen fraction 5(100 μg/infection) | 908.5 |
| Thymosin fraction 5(100 μg/infection) | 2679.8 |
| Thymosin $\beta_3$ (1 μg/infection) | 2758.6 |
| Thymosin $\beta_3$ (10 μg/infection) | 2954.3 |

*Values in p moles ($^3$HdGTP/30 min/$10^8$ cells)

TABLE 3

Distribution of TdT activity in fractionated tissues from NIH Swiss nu/+ and nu/nu mice

| | BSA fractions | | | | | | | |
|---|---|---|---|---|---|---|---|---|
| | A | | B | | C | | D | |
| | I | II | I | II | I | II | I | II |
| Thymus NIH nu/+ | 185* | 7 | 193 | 3 | 161 | <0.1 | <0.1 | <0.1 |
| Bone marrow NIH nu/+ | 145 | <0.1 | 6 | <0.1 | 1 | <0.1 | <0.1 | <0.1 |
| Bone marrow NIH nu/nu | 16 | 3 | <0.1 | 1 | 1 | <0.1 | <0.1 | <0.1 |

*Picomoles of dGTP incorporated/hour/$10^8$ cells.

As illustrated in Table 3, TdT activity is evenly distributed in fractions A, B and C of BSA gradient fractionated thymocytes. These fractions contain 80% of the initial thymocytes. Using NIH Swiss thymocytes, only the peak I TdT activity was detectable, which is consistent with previous data demonstraing an age- and strain-dependent difference in peak II TdT expression. In contrast to thymocytes, however, fractionated bone marrow cells from NIH Swiss mice primarily had TdT activity associated with fraction A. Although this reaction constitutes only 5% of the total bone marrow, the specific activity of TdT in these cells was comparable to thymocytes suggesting that the majority of the cells in fraction A are TdT-positive. Also shown in Table 3 are the results obtained with bone marrow from NIH Swiss nu/nu mice. In contrast to the thymic-bearing NIH Swiss mice, only approximately 10% of the TdT activity was detectable. Comparable results (not shown) have been obtained with C57BL/6 mice in that TdT is found in the A, B, and C fractions of thymus cells, while only fraction A of bone marrow cells expresses TdT. Similarly, thymectomy of four-week-old C57BL/6 mice is followed by a rapid decrease of TdT-positive cells in the bone marrow. These results demonstrate that TdT is associated with most thymocyte subpopulations and a minor bone marrow population, presumably a prothymocyte population, and that the latter population may be under thymic regulation.

The restortation of various T cell fractions and the regulation of T cell differentiation of bone marrow cells have been shown to be influenced by thymic hormones. One such effect has been the ability of thymosin fraction 5 to induce the expression of theta in vivo. The BSA gradient fractions of bone marrow cells were therefore examined for the expression of theta and for their inducibility for theta expression. As shown in Table 4, the majority of bone marrow cells are theta-negative by immunofluorescence including the A fraction which is TdT-positive.

TABLE 4

Expression of Thy-1 in fractionated bone marrow cells from C57BL/6 mice before and after in vitro incubation with thymosin fraction 5

| | Percent fluorescent cells* BSA fractions | | | |
|---|---|---|---|---|
| | A | B | C | D |
| Bone marrow before thymosin | 3.5 | 2.5 | 1.3 | 2.5 |
| Bone marrow after thymosin | 66.6 | 11.3 | 1.5 | 3.0 |

*Thy-1-positive cells were determined by indirect immunofluorescence as described in the Materials and Methods.

These results demonstrate that TdT and theta antigen expression are independent and that TdT expression may precede theta expression in T cell differentiation. However, if fractionated bone marrow cells are incubated in vitro with thymosin fraction 5, the A fraction is inducible for theta expression. These results are consistent with previous studies suggesting that thymic hormones induce theta expression in TdT-positive bone marrow cells.

In order to next examine the effect of thymosin fraction 5 on TdT expression, NIH Swiss nu/nu mice were treated with thymosin fraction 5 and assayed fractionated bone marrow cells for TdT activity. As shown in Table 5, ten daily injections of 100 µg of thymosin fraction 5 increased TdT activity in the bone marrow fraction A to levels comparable to their heterozygous littermates.

TABLE 5

In vivo induction of TdT activity in bone marrow cells from nude mice with thymosin fraction 5*

| | BSA fraction | | | | | | | |
|---|---|---|---|---|---|---|---|---|
| | A | | B | | C | | D | |
| | I | II | I | II | I | II | I | II |
| Saline | 22+ | 4 | 9 | 1 | <0.1 | <0.1 | <0.1 | <0.1 |
| Spleen fraction 5 | 18 | <0.1 | 10 | <0.1 | 3 | <0.1 | <0.1 | <0.1 |
| Thymosin fraction 5 | 210 | 3 | 32 | <0.1 | 3 | <0.1 | 2 | <0.1 |

*NIH Swiss nu/nu were given 10 daily injections of spleen fraction 5, thymosin fraction 5 or saline intraperitoneally. Twenty-four hours after the last injection, the mice were sacrificed and TdT was isolated as described in the Materials and Methods.
+ Picomoles of dGTP incorporated/hour/$10^8$ cells.

The induction is specific for thymosin fraction 5 in that neither saline nor spleen fraction 5 treatment had any effect. Interestingly, thymosin treatment of NIH Swiss nu/nu mice resulted in the appearance of peak I activity; however, when the same treatment is given to thymectomized C57BL/6 mice, both peaks I and II were induced to a specific activity comparable to that of the normal controls. No TdT activity was detected in fractionated cells from either the spleen or lymph nodes of thymosintreated mice. The results obtained after in vivo treatment with thymosin suggested that this hormone could promote TdT expression in bone marrow. However, it was not possible to differentiate between a direct inductive effect and a secondary effect on differentiation. Therefore the ability of thymosin fraction 5 to induce TdT in vitro in fractionated bone marrow and spleen cells from NIH Swiss nu/nu mice was examined. When fractionated spleen cells were treated with 25 ng/ml of thymosin fraction 5 for 18 hours, TdT was specifically induced in fraction B of bone marrow cells. Again, only peak I activity was induced. This time, however, the specific activity obtained was about 60% of the normal bone marrow fraction A population. Spleen fraction 5 had no inductive effect in vitro. These results, therefore, suggest a direct role of thymosin fraction 5 in the induction of TdT activity in the bone marrow cells from nu/nu mice.

The induction using 25 ng/ml in vitro is rapid such that within two hours a significant increase in TdT is evident. By four to six hours the cells are fully induced, and the enzyme activity remains constant up to 24 hours. The results obtained at 12 hours in the presence of 0.5 µg/ml of actinomycin D indicated that greater than 95% of the RNA synthesis is inhibited, as is the induction of TdT.

Since thymosin fraction 5 is a mixture of several different peptides, the ability of several purified peptides to induce TdT in vitro in BSA fraction B from the bone marrow was determined. As shown in Table 6, most of the peptides did not induce TdT. However, in the $\beta$ group, $\beta_4$ was able to induce TdT to 30% of the thymosin fraction 5 level and $\beta_3$ had the highest activity and induced TdT to values close to 80% of that obtained with thymosin fraction 5.

TABLE 6

In vitro induction of TdT in fraction B bone marrow cells from NIH Swiss nu/nu mice

| Treatment | TdT specific activity* |
|---|---|
| Control saline | 2.0 |
| Spleen fraction 5 | 1.0 |
| Thymosin fraction 5 | 214.0 |
| α-1 | 5.2 |
| β1 | 2.5 |
| β3 | 145.0 |
| β4 | 58.0 |
| Synthetic α-1 | 3.0 |

*Values for peak I activity only (picomoles $^3$HdGTP/hour/$10^8$ cells). Incubation was for 18 hours with 50 ng/ml of each peptide.

Figure 3:
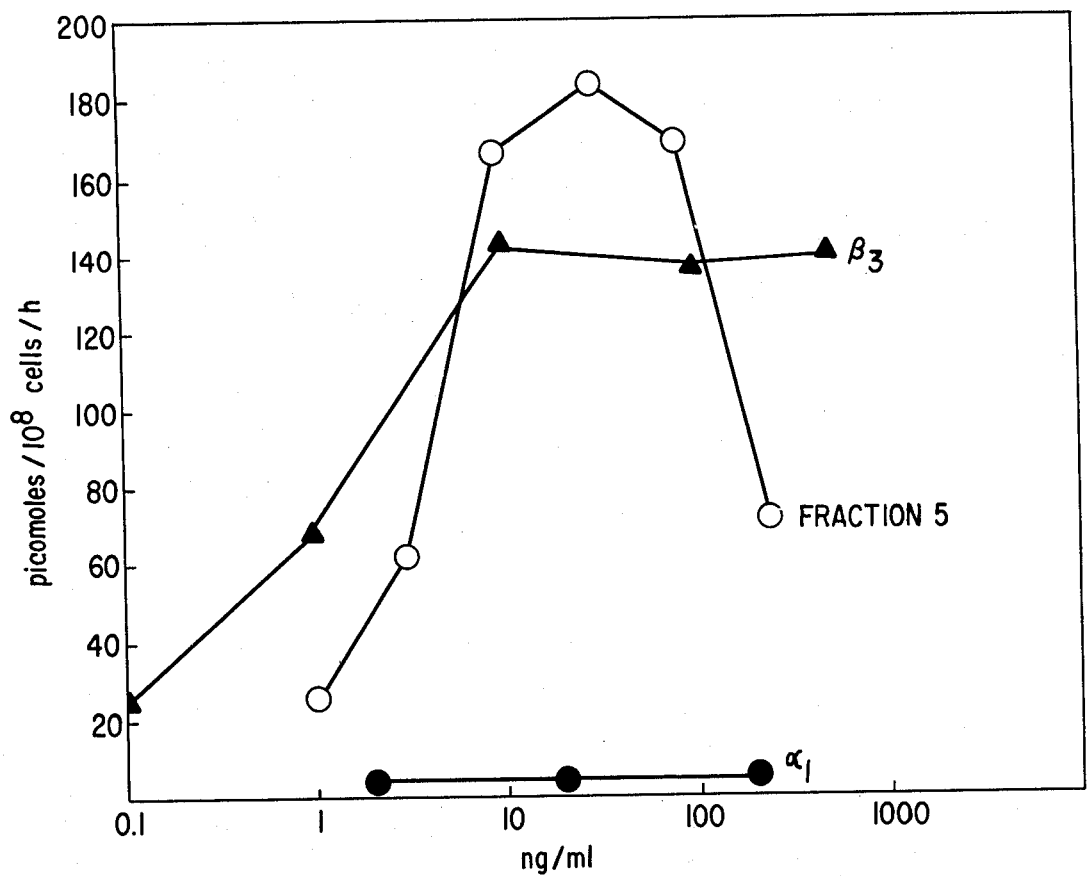

The concentration dependence for the induction of TdT in bone marrow fraction B cells by thymosin fraction 5, $\alpha_1$ and $\beta_3$ is shown in FIG. 3. For thymosin fraction 5, concentrations as low as 3 ng/ml had a significant effect and approximately 30 ng/ml was optimal; however, at higher concentrations, there was a significant inhibitory effect, which was not associated with a loss of cell viability. In contrast, $\alpha_1$ did not show any induction at concentrations ranging from 2 to 200 ng/ml. $\beta_3$ showed significant TdT induction at 1 ng/ml and the optimum was achieved at 10 ng/ml. In contrast to thymosin, however, no inhibition of induction was observed even at concentrations of 500 ng/ml. These results suggest that thymosin fraction 5 and $\beta_3$ specifically induce TdT in a manner comparable to the induction observed for other enzymes in response to specific hormones.

Thymosin $\beta_3$ and thymosin $\beta_4$ may be administered to warm blooded mammals by parenteral application either intravenously, subcutaneously or intramuscularly.

The compounds are immunopotentiating agents with a daily dosage of $\beta_3$ in the range of about 1 μg/kg to 50 μg/kg and of $\beta_4$ in the range of about 30 μg/kg to 150 μg/kg of body weight per day for intravenous administration. Obviously the required dosage will vary with the particular condition being treated, the severity of the condition and the duration of the treatment. A suitable dosage form for pharmaceutical use is 4 mg of lyophilized thymosin $\beta_3$ or 12 mg of lyophilized thymosin $\beta_4$ per vial to be reconstituted prior to use by the addition of sterile water or saline.

Also included within the scope of the present invention are the pharmaceutically acceptable salts of thymosin $\beta_3$ and $\beta_4$ such as the alkali metal salts, e.g., the sodium or potassium salts, or the salts of strong organic bases such as guanidine. In addition, the counter ions of these cations as well as of lysine residues in thymosin $\beta_3$ or $\beta_4$ such as the hydrochloride, hydrobromide, sulfate, phosphate, maleate, acetate, citrate, benzoate, succinate, malate, ascorbate and the like, may be included in the preparation.

We claim:

1. Thymosin $\beta_3$ being a polypeptide essentially free of other thymic polypeptides and having the following amino acid sequence:

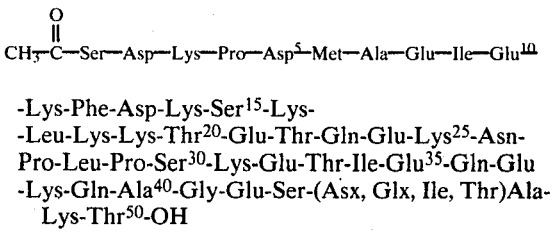

-Lys-Phe-Asp-Lys-Ser$^{15}$-Lys-
-Leu-Lys-Lys-Thr$^{20}$-Glu-Thr-Gln-Glu-Lys$^{25}$-Asn-
Pro-Leu-Pro-Ser$^{30}$-Lys-Glu-Thr-Ile-Glu$^{35}$-Gln-Glu
-Lys-Gln-Ala$^{40}$-Gly-Glu-Ser-(Asx, Glx, Ile, Thr)Ala-
Lys-Thr$^{50}$-OH and the pharmaceutically acceptable acid addition salts or base salts thereof.

2. Thymosin $\beta_4$ being a polypeptide essentially free of other thymic polypeptides and having the following amino acid sequence:

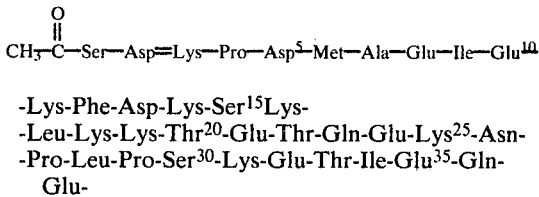

-Lys-Phe-Asp-Lys-Ser$^{15}$Lys-
-Leu-Lys-Lys-Thr$^{20}$-Glu-Thr-Gln-Glu-Lys$^{25}$-Asn-
-Pro-Leu-Pro-Ser$^{30}$-Lys-Glu-Thr-Ile-Glu$^{35}$-Gln-Glu-
-Lys-Gln-Ala$^{40}$-Gly-Glu-Ser-OH and the pharmaceutically acceptable acid addition salts or base salts thereof.

* * * * *

UNITED STATES PATENT AND TRADEMARK OFFICE
CERTIFICATE OF CORRECTION

PATENT NO. : 4,297,276
DATED : October 27, 1981
INVENTOR(S) : Allan L. Goldstein et al.

It is certified that error appears in the above—identified patent and that said Letters Patent is hereby corrected as shown below:

On The Title Page item (73) should read

-- George Washington University, Washington, D. C. --.

Signed and Sealed this

Eleventh Day of May 1982

[SEAL]

Attest:

GERALD J. MOSSINGHOFF

Attesting Officer

Commissioner of Patents and Trademarks